United States Patent
Klein et al.

(10) Patent No.: US 6,793,491 B2
(45) Date of Patent: Sep. 21, 2004

(54) STABILIZING IMPLANT SYSTEM (75) Inventors: Michael Klein, Woodmere, NY (US); Michael Abrams, Roslyn, NY (US)

(73) Assignee: Implant Logic Systems, Cedarhurst, NY (US)

( * ) Notice: Subject to any disclaimer, the term of this patent is extended or adjusted under 35 U.S.C. 154(b) by 0 days.

(21) Appl. No.: 10/093,368

(22) Filed: Mar. 7, 2002

(65) Prior Publication Data

US 2002/0177104 A1 Nov. 28, 2002

Related U.S. Application Data (60) Provisional application No. 60/274,305, filed on Mar. 8, 2001.

(51) Int. Cl.[7] .............................. A61C 8/00; A61C 19/04
(52) U.S. Cl. .............................. 433/173; 433/72; 433/75
(58) Field of Search .............................. 433/72, 75, 76, 433/173

(56) References Cited

U.S. PATENT DOCUMENTS

| | | | | |
|---|---|---|---|---|
| 5,320,529 A | * | 6/1994 | Pompa | 433/76 |
| 5,350,297 A | * | 9/1994 | Cohen | 433/76 |
| 5,769,636 A | * | 6/1998 | Di Sario | 433/213 |
| 5,967,777 A | | 10/1999 | Klein et al. | 433/75 |
| 6,319,000 B1 | * | 11/2001 | Branemark | 433/75 |

* cited by examiner

Primary Examiner—John J Wilson
(74) Attorney, Agent, or Firm—Katten Muchin Zavis Rosenman (57) ABSTRACT

A system of temporary stabilizing implants are provided at specifically determined locations in a patient's jawbone for positioning and temporarily stabilizing a dental surgical template at a specifically determined orientation with respect to the jawbone. The template is used to arrange and create osteotomies at sites where permanent dental implants will be located. The template is removably and replaceably positioned with respect to the temporary stabilizing implants by the use of components provided in the template that engage the temporary stabilizing implants, such that the template may be used over a prolonged time period as necessary. Once the dental surgical template is no longer needed, the temporary stabilizing implants are preferably removed.

13 Claims, 9 Drawing Sheets

STABILIZING IMPLANT SYSTEM

CROSS-REFERENCE TO RELATED APPLICATION

This application claims the benefit under 35 U.S.C. §119 (e) of provisional application 60/274,305 filed Mar. 8, 2001.

FIELD OF THE INVENTION

This invention relates to an apparatus for stabilizing dental surgical templates generally, and more particularly, to an implant system for positioning and temporarily stabilizing a removable and replaceable dental surgical template at a specifically determined orientation with respect to the patient's jawbone, and allowing for the removal and later reintroduction and repositioning of such template relative to such determined location.

BACKGROUND OF THE INVENTION

When installing dental implants into a patient's jawbone, especially when numerous teeth must be replaced or created, it is advantageous to use a dental surgical template to aid in the positioning and orientation of the dental implant drill with respect to the jawbone. The surgical template is typically comprised of a plastic, acrylic or vinyl replica of the prospective teeth to be supported by dental implants. The surgical template is then modified and readied for surgical use by manually cutting holes in the approximate and prosthetically-desirable areas where the surgeon anticipates he or she will place dental implants. These holes are made large enough to accommodate the passage of a dental implant drill, bur and/or guide pin.

Initially, indications are made on the template where the teeth are to be located. Such templates and markings used to be made by the dentist directly in the mouth based upon his own estimation. Recently computer programs have been available to assist in creating such indications.

For instance, radiopaque markers may be applied to the surgical template by applying a radiopaque material (e.g.: barium sulfate, gutta percha, silver powder-acrylic mixture, etc) to or below the surface of the replica teeth of the template to create what is generally known as a CT scan appliance. These radiopaque markers demonstrate the tooth outline and/or position of the prospective tooth or teeth to be implanted on a CT scan image. The patient wears the CT scan appliance and obtains a CT scan of the jawbone prior to having dental implant surgery. The radiopaque markers of the CT scan appliance would be readily discernible on the CT scan images and thus allow the surgeon or dentist to evaluate the available bone relative to the radiopaque tooth position markers at the proposed implant site. Currently available software, e.g. SIM/PLANT manufactured by Columbia Scientific, Inc. of Columbia, Md., reformats such CT scan data into 2- and 3-dimensional images that allow for interactive evaluation of the jawbone at proposed implant sites and surgical treatment planning by the dental implant therapist. The software further enables the dental implant therapist to perform a dental implant simulation directly on to the reformatted CT scan images. In essence, the implant surgeon can create a simulated dental implant surgical treatment plan or surgical blueprint on the patient's CT scan images.

In U.S. Pat. No. 5,967,777, a method is described by which the three dimensional data coordinates of the above described simulated dental implant positions are transferred to a CNC milling machine that precisely mills and cuts holes into the CT scan appliance to create a surgical template. This precision computer-milled surgical template is then mated with drill guide components that precisely and accurately guide the drilling or osteotomy (i.e., drilled hole in the jawbone) creation process used at the time of dental implant surgery. It is even possible, under certain circumstances, to actually insert the dental implant through this computer-milled surgical template assembly and directly into the patient's jawbone. When this computer-milled precision surgical template assembly is refitted to the patient's mouth at the time of implant surgery, the surgeon's drill is precisely guided to create implant osteotomies that accurately correspond in three dimensional position and trajectory to the simulated implant positions of the pre-surgical computerized surgical blueprint treatment plan.

When using any surgical template to assist in the drilling of dental implant osteotomies, it is generally desirable for the surgical template to be stable as well as removable and accurately repositionable in the patient's mouth. If the surgical template is not stable, then the accuracy of the drilling process may be compromised, possibly leading to poor implant positioning and/or injury to the patient. Surgical template stability and/or fixation is required to reduce surgical drilling error and enhance proper implant positioning.

The computer-milled surgical template assembly described in U.S. Pat. No. 5,967,777 requires absolute stability during its use. This template assembly is usually supported and stabilized by the patient's existing teeth or sometimes a combination of teeth and other prosthetically-restored teeth or implants. However, in the absence of adequate existing support required to provide necessary stabilization (e.g. in the case of complete edentulism), a method to provide such required support and stabilization is needed.

It is an object of the present invention to provide for a system and method of stabilizing, securing and/or fixing a template in the mouth that is accurately positionable at the time of the dental implant drilling/osteotomy creation process. Furthermore, if it is necessary to remove the template from the mouth at a later time, the system of the invention will allow for the reproducibly accurate and stable reintroduction of this template to the same fixed position and orientation relative to the patient's jawbone.

The present solution is to form holes in the template and through these holes drill osteotomies that will subsequently receive a temporary stabilizing implant (TSI). Once the TSI is inserted into the jawbone of the patient, a component system is used to attach the surgical template to the TSI and thus secure, stabilize and/or fix said surgical template to the patient's jawbone.

These holes and TSI's would be typically spaced and positioned sufficiently around the template to support and stabilize it. Typically two to three TSI locations would be sufficient to adequately support and stabilize the template.

Once the template is stabilized, the osteotomies for the permanent dental implants can be accomplished and permanent dental implants can be installed into the bone. If the surgical template is no longer required following this implant placement, then the TSI's can be removed. Alternatively, if it will be necessary for the surgical template to be accurately and securely reintroduced to the patient's mouth at a later time, the TSI's would be retained and eventually removed when the surgical template was no longer necessary.

The TSI's may vary in function and appearance depending on the type of template required and the nature of the dental situation. The TSI's provide a stable foundation for the accurate repositioning of the removable surgical template back into the mouth at any later time as required by the specific situation.

It should be noted that there are other existing methods, technologies under development and/or technological methods and/or devices yet to be developed that do and/or will require stabilization and/or fixation of a dental surgical template or device to the patient's jawbone. It is the purpose of this invention to provide for the necessary stabilization and/or fixation for those entities as well.

The temporary stabilizing implant system of the present invention could also be used to temporarily stabilize and support a fixed provisional (temporary) bridge or other fixed provisional dental prosthesis.

OBJECTS OF THE INVENTION

It is an object of the present invention to provide a stabilizing implant system for accurately positioning a dental surgical template at a specifically determined orientation with respect to the patient's jawbone.

It is a further object of the present invention to provide at least one, or a plurality of, temporary stabilizing implants that are placed into and temporarily located in a patient's jawbone for the purpose of providing support, stabilization and/or fixation of a surgical template.

Still other objects and advantages of the invention will become clear upon review of the following detailed description in conjunction with the appended drawings.

SUMMARY OF THE INVENTION

A system of stabilizing implants are provided at specifically determined locations on a patient's jawbone for positioning and temporarily stabilizing a dental surgical template at a fixated and stabilizing orientation with respect to the jawbone. The dental surgical template is provided with components that allow the accurate reproducible mechanical integration of said template to the system of implants. Once said surgical template is secured and fixed to the temporary stabilizing implants, the template may be used to create osteotomies in a patient's jawbone at locations where more permanent dental implants will be installed. The temporary stabilizing implants allow for the subsequent removal and accurate repositioning and fixation of the surgical template to allow for the accurate position the surgical template during a variety of successive time periods. Once the osteotomies have been created and the dental implants installed, and/or the dental surgical template is no longer needed to plan and/or verify the location of the implant surgery, the temporary stabilizing implants may be removed from the patient's jawbone.

DETAILED DESCRIPTION OF THE PREFERRED EMBODIMENTS

The following detailed description is of the best mode or modes of the invention presently contemplated. Such description is not intended to be understood in a limiting sense, but to be an example of the invention presented solely for illustration thereof, and by reference to which in connection with the following description and the accompanying drawings one skilled in the art may be advised of the advantages and construction of the invention. In the various views of the drawings, like reference characters designate like or similar parts.

Figure 1:
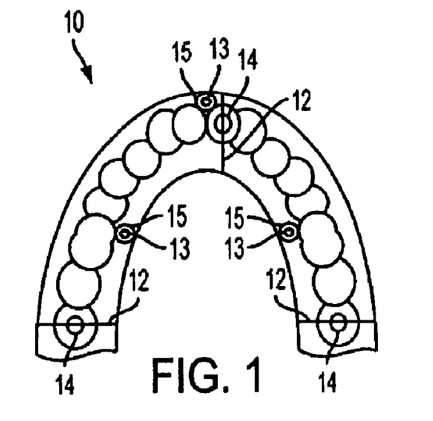
FIG. 1 is a top view of a typical dental template.
Figure 2:
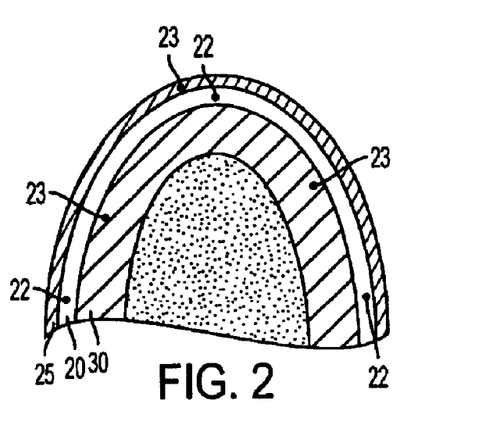
FIG. 2 is a top view of a representative patient's lower jawbone with stabilizing implant positions noted thereon.

FIG. 1 is a top view of a surgical dental template 10 created using methods known in the art, and FIG. 2 is a top view of a patient's lower jawbone 20 surrounded by gum tissue 25 and 30 on either side of the jawbone. Typically, markings 12 are made on the template 10 at the locations 22 (see FIG. 2) where drilling is to occur in the jawbone and where implants and dental prosthesis will be placed. The markings 12 may correspond to each tooth location, or only select locations corresponding to selected implant sites. Such markings 12 can be created automatically using CT scan data as described above, or by other ways known in the art. In accordance with the system of the present invention, the dental template 10 might also initially be marked at two or three locations 13 corresponding to the locations 23 (FIG. 2) of the temporary stabilizing implants (to be discussed later). Such template 10 might also have other markings corresponding to permanent implant sites that will ultimately be covered by dental prosthesis. However, the temporary stabilizing implants of the present invention will preferably not ultimately be covered by dental prosthesis, but will instead be removed when the dental template is no longer needed.

The concepts of "temporary" stabilizing implants and "permanent" dental implants as described herein refers to the nature of the implants during certain temporal periods. Initially, the surgical template is stabilized with respect to a person's jawbone by "temporary" stabilizing implants, such implants having an initial primary purpose of orienting and fixing the template in a specifically determined location. Such temporary implants may be located at implant sites that have no relation to future dental prosthesis, i.e., "permanent" dental implant sites, or such implants may be located at implant sites that will eventually receive the installation of "permanent" dental implants and permanent dental prosthesis thereon. In other words, the installation sites of the temporary stabilizing implants in the patient's jawbone may be used initially to receive temporary stabilizing implants, and then may be used again to receive "permanent" dental implants as the need arises. Of course, the location of the implant site may dictate the nature of the site and type of implant installed thereon.

Returning to FIGS. 1 and 2, after the surgical template 10 has been marked, holes or openings 15 in the template 10 corresponding to the temporary stabilizing implant positions 23 are provided to enable a dentist or surgeon to properly locate the implant positions 23 along the jawbone 20. Such openings 15 may be created by hand, or as noted above in the '777 patent, a milling machine may be used to automatically drill the necessary holes in the template 10 corresponding to where the stabilizing implants will be placed to facilitate the drilling of the holes in the jawbone 20 at the temporary implant positions 23. Other methods of creating the openings 15 are contemplated.

Once the surgical template 10 is properly positioned such that the holes 15 are aligned with the stabilizing implant positions 23, the doctor positions the surgical template 10 on or in relation to the jawbone and drills through the holes 15 in the surgical template 10 and into the jawbone 20 at the implant positions 23. While FIG. 2 shows three temporary stabilizing implant positions 23, only two positions or even one position may be necessary to properly stabilize the template, and more than three positions may be used if desired. Also, while it is critical when drilling holes 14 for the installation of "permanent" dental implants that will eventually be covered by dental prosthesis that such holes 14 be at an appropriate angle with respect to the jawbone, the holes 15 drilled for the insertion of the stabilizing implants of the present invention do not have to be that precise or accurate. In fact, the holes 15 can even be drilled at an angle and without the aid of initial positioning markers 13 as long as such holes 15 are adequate to support a stabilizing implant and a dental template 10 seated thereon. Furthermore, while the temporary stabilizing implant positions 23 are shown at various locations on the jawbone, it will be understood that such positions 23 could be located where permanent teeth are not present, or at other locations along the jawbone from where teeth would not normally project. In addition, as discussed above, the sites 22 for permanent dental implants can also be used initially as sites for temporary stabilizing implants.

Figure 3:
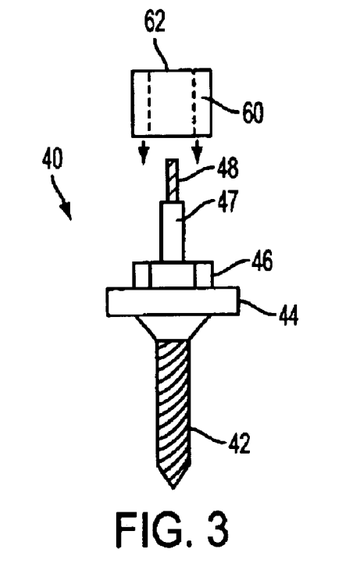
FIG. 3 is a side view of a one-piece embodiment of the stabilizing implant of the present invention.
Figure 4:
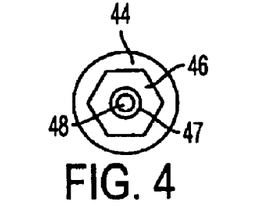
FIG. 4 is a top view of the implant of FIG. 3 without the sleeve.

A one-piece embodiment 40 of a temporary stabilizing implant of the present invention is shown in FIG. 3 (side view) and FIG. 4 (top view), and comprises a lower threaded portion 42 for insertion into a jawbone, a platform 44, an engagement portion 46 for engagement by a standard driver (not shown), and a stem 47 having a threaded portion 48 extending upwardly therefrom. In operation, the surgical template 10 is placed on the jawbone 20, the holes are drilled in the jawbone, and the temporary stabilizing implant 40 is inserted through a hole 14 in the template 10 and installed into the jawbone area 20 (see FIG. 2) using a standard driver (not shown). Thereafter, a sleeve 60 having a cylindrical bore 62 therethrough is slid downwardly over the stem 47 until the sleeve 60 comes to rest upon the engagement portion 46 of the implant 40. Alternatively, the sleeve 60 can have a bore 62 that is configured to engage the engagement portion 46 of the implant 40, in which case the sleeve 60 can be firmly planted with respect to the temporary stabilizing implant 40. However, it is preferable that the sleeve 60 have the ability to move slightly with respect to the implant 40 to account for variations in part tolerances and implant installation positions. This process is repeated until a temporary stabilizing implant 40 has been inserted at each of the appropriate implant positions 23 (see FIG. 2).

Figure 5:
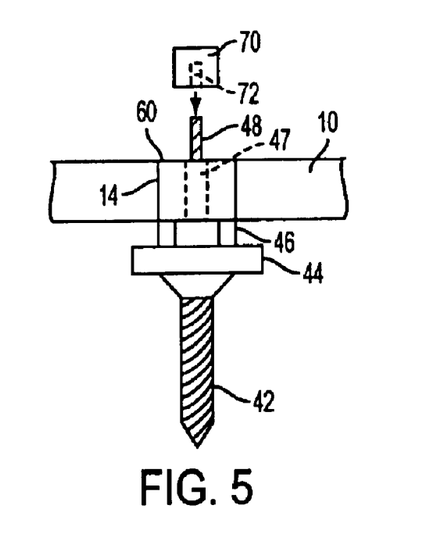
FIG. 5 is a side view of a one-piece embodiment of the stabilizing implant of the present invention with a portion of a dental template shown attached thereto.

As shown in the embodiment of FIG. 5, the surgical template 10 is then pressed down onto each sleeve 60 and the sleeve is then luted or cemented in place to the template 10 within the hole 15 used for drilling. Other equivalent methods of fixing the template to the sleeve may be used as described below. For example, the sleeve 60 can first be cemented or luted to the template 10 within the hole 15 using manual or mechanical means, after which the template 10 with the sleeves 60 embedded therein would be located in the patient's mouth by engagement of the sleeves 60 with the stems 47, and/or engagement members 46 of the stabilizing implants 40. The surgical template 10 is then rendered removable and replaceable, capable of sliding on and off of the implant 10 as necessary. The template 10 is then capable of being secured in place to the top of the implant 40 by means of a nut 70 having an inwardly threaded section 72 that mates with the threaded section 48 of implant 40. This represents a significant advancement in the art, since it is common practice to temporarily cement templates in place, which causes problems when it is time to remove them from the patient's mouth. By attaching the surgical template 10 to the sleeves 60 of the stabilizing implants 40, the template 10 may be temporarily positioned in the mouth, removed therefrom, and repositioned at a later time in the exact same location, all without unnecessarily permanently affixing the template 10 to the jawbone 20.

Figure 6:
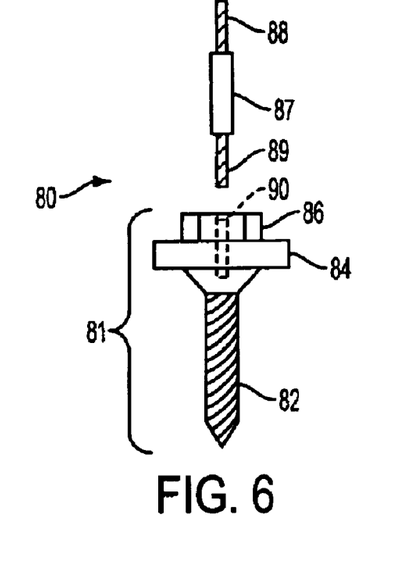
FIG. 6 is a side view of a two-piece embodiment of the stabilizing implant of the present invention.

As noted above, the system of stabilizing implants of the present invention can be utilized when the template 10 is to be located and positioned at the very beginning of the process before a CT scan is taken. Again, in such a situation, all the doctor needs to do is take a blank template and drill holes 15 wherever he wants so that they will not interfere with the actual or "permanent" dental implants located in their positions 22 (see FIG. 2) along the jawbone that will eventually be covered by dental prosthesis. In this case, the doctor would preferably use a two-piece embodiment stabilizing implant 80 as shown in FIG. 6. The two-piece stabilizing implant 80 comprises a lower portion 81 defined by a lower threaded portion 82 for insertion into a jawbone, a platform 84, an engagement portion 86 for engagement by a standard driver (not shown), and a removable stem 87 having an upper threaded portion 88 and a lower threaded portion 89 each extending outwardly from the stem body. In operation, once the holes in the jawbone have been made, the lower portion 81 of the stabilizing implant 80 is inserted through a hole 14 in the template 10 and screwed into the bone area using a standard driver (not shown). Thereafter, the stem 87 would be screwed into the threaded bore 90 of the lower portion 81 of the stabilizing implant 80 so as to form the upper stem portion. Thereafter as before, a sleeve 60 is slid downwardly over the stem 87 until the sleeve 60 comes to rest upon the engagement portion 86 of the implant 80. This process is repeated until a stabilizing implant 80 has been inserted at each of the appropriate implant positions 23 (see FIG. 2). The surgical template 10 is then slid over and secured to the sleeves by luting or the like as described in connection with the one-piece embodiment of FIGS. 3–5, and then secured in place by means of a nut 70 as also described above. Alternatively, as described below, the sleeve 60 may first be embedded in the template 10 prior to engagement of the template 10 with the implants 80. In the embodiment illustrated in FIG. 6, the dentist can remove the template 10 by undoing the nut 70, lifting off the template 10 from the top stem 87 and then unscrewing the top stem 87 leaving the bottom portion 81 of the implant 80 in place. This bottom portion 81 will therefore remain as a stabilizing implant in place when later he gets the template 10 back from the lab and puts the template 10 back for the actual drilling of the holes 22 for the permanent dental implants that will be covered by dental prosthesis.

The one- or two-piece embodiment of the stabilizing implant of the present invention can be used even if a CT scan or MRI is not used to pre-mark and/or pre-drill the dental template, particularly since the temporary stabilizing implant locations 23 will preferably differ from the more permanent dental implant locations 22 as shown in FIG. 2. The two-piece embodiment 80 of FIG. 6 is preferable in connection with stabilizing implant locations 23 near the back teeth. A one-piece stabilizing implant 40, for example, would be difficult to drive into the jawbone near the back of the mouth because the height of the stem 47 combined with the height of the driver (not shown) would likely make it very difficult for the patient to open his/her mouth to accept such equipment therein. However, by using the two-piece embodiment of FIG. 6, the doctor can insert the lower portion 81 of the stabilizing implant 80 with a shorter driver, screw the lower portion 81 in place and then screw the stem 87 in by hand or with a small additional driver (not shown).

Although the basic purpose of the implant of the invention is a temporary stabilizing implant for stabilizing a dental surgical template, an additional use for such implants could be for a temporary implant system. Typically, dental implants are put in the mouth, and as heretofore explained, remain there for a number of months until they are ossified with the jawbone. However, in that case, the person remains without any teeth for a good period of time. It has therefore been suggested to provide a temporary implant system for securing a temporary bridge or temporary teeth during the healing period of the standard implants. In such temporary implant systems, it is known to simply screw a small implant in place and place a temporary bridge on it, and so long as it supports weight, it will be sufficient. There is no interest in making sure that this temporary implant ossifies and it is just temporarily there. When the regular implants are put in, these temporary ones are then removed.

The present two-piece embodiment of the stabilizing implant of the invention can likewise be used for such purpose. Namely, the lower portion 81 is first inserted into a jawbone. Thereafter, the upper stem 87 is screwed into the lower portion 81 and a temporary bridge (not shown) having an equivalent structure as the dental surgical template 10 described herein is placed on the upper stem portion 87 again by means of a sleeve 60 secured within the temporary bridge. The temporary bridge can then be held in place by means of a nut 70 on top. Typically, a hole or recess similar to hole 15 in dental template 10 would be made in the bridge so that the nut would not project beyond the surface of the bridge and would not interfere with chewing during the healing period.

Figure 7:
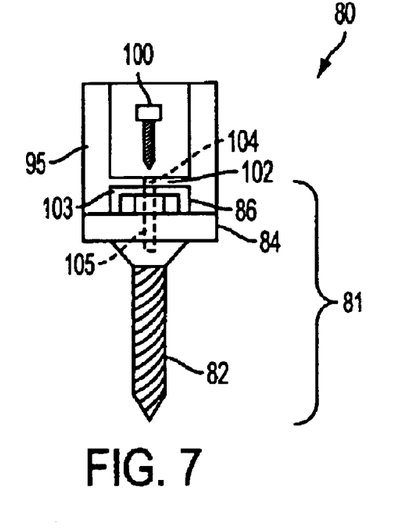
FIG. 7 is a side view of an alternative embodiment of the stabilizing implant of the present invention shown with a coping screw used to fix a sleeve to the implant.

In an alternative embodiment of the present invention, instead of using a nut 70 to secure a template 10 or a temporary bridge (not shown) onto the stem 87, a standard coping screw 100 that is insertable into a bore 105 on the lower portion 81 of the implant 80 can be used as shown in FIG. 7. A preferably round sleeve 95 having a raised floor 102 with a hole 104 therethrough, would be placed directly over the preferably hex-shaped engagement head 86 so that the head 86 is covered by a circular recess 103 and the raised floor 102, with the recess 103 circumscribing the head 86 so that it will not be held in place by the head 86 but will permit slight movement so that the bridge or template 10 can properly be positioned (not shown in FIG. 7) in the patient's mouth. In the one-piece embodiment of FIGS. 3–5, the sleeve 95 is hollow from end to end and rests upon the head 46 and is not circumscribed thereabout, but is stabilized by the engagement of the sleeve 95 with the stem 47 and is secured by means of a nut 70. In the embodiment of FIG. 7, the sleeve 95 is secured in place by the head 86 and the passage of a coping screw 100 through the orifice 104 in the sleeve 95 and through the head 84 and finally into the lower portion 105 of the implant 80. The temporary bridge or template would then be secured to the sleeves as discussed above, or alternatively the sleeves would be initially secured to the temporary implant prior to the application of the bridge or template to the implants, and then such bridge or template would be temporarily secured to the implant system of the present invention by coping screws.

The benefit of using the implant of FIG. 7 for a temporary implant system as compared with prior art systems is that in the prior art systems the temporary bridge is cemented to the implants. As a result, during subsequent visits, in order to access the gum area it is necessary to pull out the temporary bridge with the implants. In the present system, the temporary template or bridge is not cemented to the implant. Instead, as discussed in connection with a one-piece embodiment (see FIGS. 3–5), the stabilizing implant is secured by means of the sleeve 60 which slides on the upper stem 47 and then uses a nut 70 on top to hold the bridge or template in place. Or, as discussed in connection with a two-piece embodiment (see FIGS. 6–7), a coping screw 100 can be used as heretofore described. In such cases, all that is necessary is to unscrew the nut or take out the coping screw and remove the temporary bridge or template giving access to the gum area. Then the bridge or temporary template can be accurately relocated and repositioned by aligning the sleeves with the stabilizing implants and then screwing it into place by means of a nut, coping screw or the like, without any unnecessary cementing or permanent affixation of the template or bridge in the patient's mouth.

FIGS. 8–20 illustrate an alternative embodiment of an implant system of the present invention. Instead of installing a temporary stabilizing implant and using a sleeve as described above to mate the temporary stabilizing implant with a dental surgical template, the dental surgical template may be provided with means for positioning a temporary stabilizing implant relative to a patient's jawbone, and means for removably engaging said template to a temporary stabilizing implant.

Figure 8:
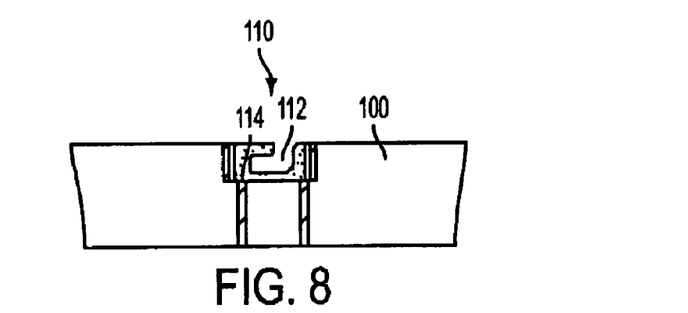
FIG. 8 is a side view of a dental template in accordance with an alternative embodiment of the present invention having a master cylinder component secured therein.
Figure 9:
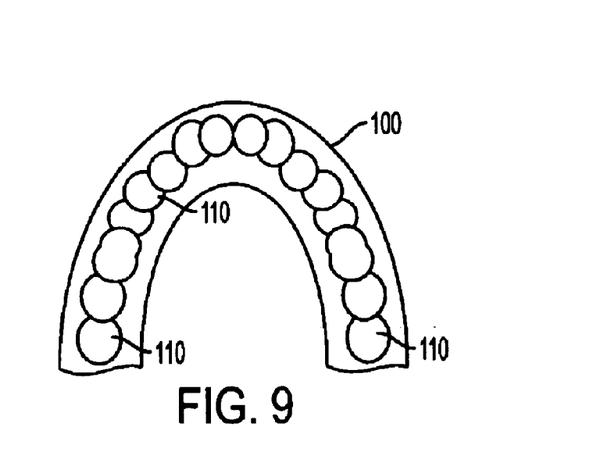
FIG. 9 is a top view of a dental surgical template illustrating the possible positioning and placement of master cylinder components.

FIG. 8 illustrates a side view and FIG. 9 illustrates a top view of a surgical template 100 of the present invention having master cylinder components 110 embedded therein for purposes of receiving integrated components as will be described below. The master cylinder component 110 is provided in specifically determined openings that coincide with the temporary stabilizing implant sites, such that temporary stabilizing implant sites can be drilled, and temporary stabilizing implants can be installed therethrough. Such openings can be prepared by hand or through the use of computer-derived data, an example of which is discussed in the '777 patent. Each cylinder 110 is secured to the template 100 by cementing or the like, although other methods of fixation are contemplated.

Figure 10:
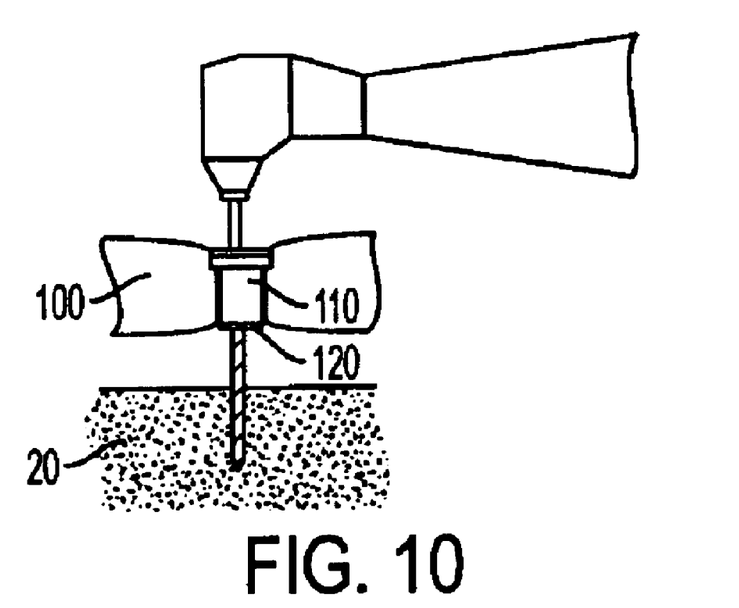
FIG. 10 illustrates the drilling of osteotomy for insertion of a temporary stabilizing implant of the present invention.
Figure 11:
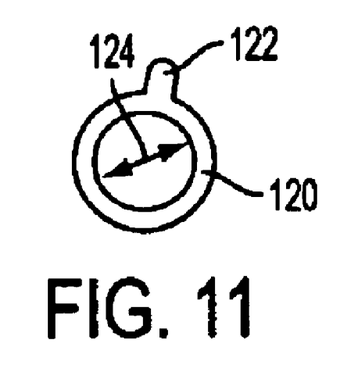
FIG. 11 is a top view of a drill guide used insertable into a master cylinder component.
Figure 12:
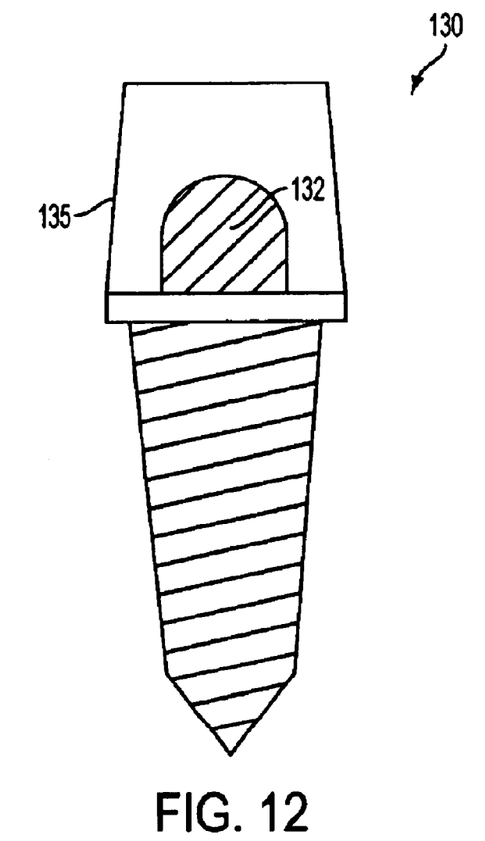
FIG. 12 is a front view of a temporary stabilizing implant of the present invention.

FIG. 10 illustrates the drilling of osteotomy for insertion of a temporary stabilizing implant into the jawbone 20 of a patient. As noted above, the surgical template is used to position and drill osteotomies for insertion of implants. With the dental surgical template of the present invention, the drilling of osteotomies is preferably facilitated through use of a drill guide 120 (FIG. 11, top view) inserted into the master cylinder 110 and rotatably secured thereto through the engagement of a drill guide key 122 with a slot 112 (FIG. 8) on the master cylinder 110. The master cylinder 110 is also provided with a shelf 114 for receiving and seating (i.e., proper placement of) portions of the integrated components. The drill guide 120 enables a surgeon to prepare an osteotomy having a desired width dimension or diameter, and also guides the attitude and direction of the drill bit during the drilling process. If a particular drilling diameter is desired, then the surgeon selects a drill guide having an appropriate internal diameter 124. Of course, while the use of a drill guide is preferred, it is not necessary.

Figure 13:
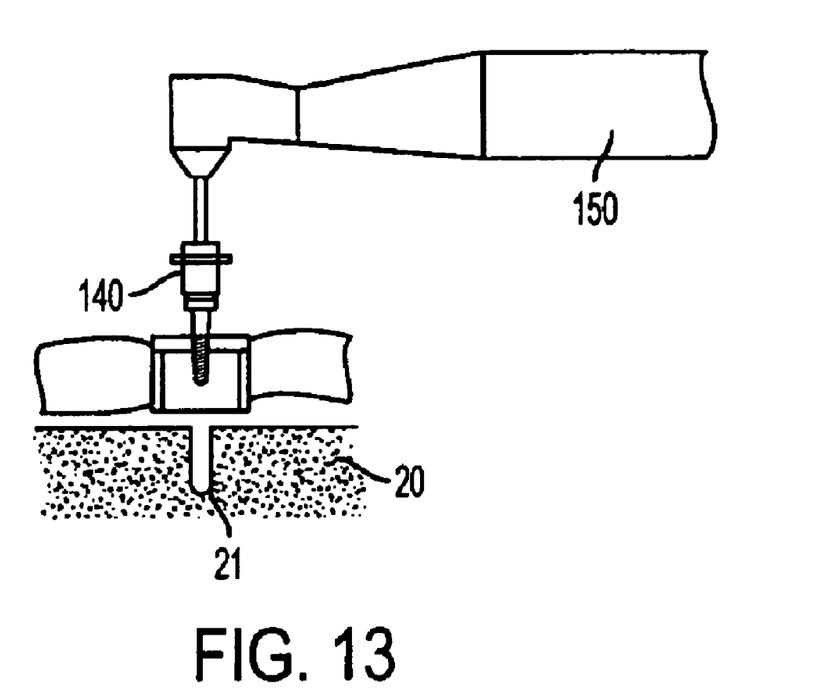
FIG. 13 illustrates the use of a driver for installing a temporary stabilizing implant.
Figure 14:
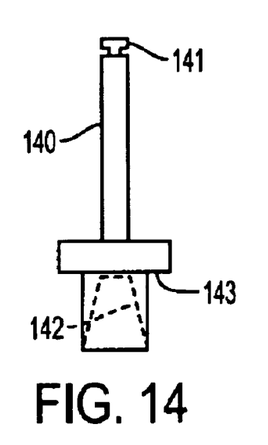
FIG. 14 is an example of a driver for installing a temporary stabilizing implant.

As shown in FIG. 13, once the osteotomy 21 is drilled, the drill guide 120 is removed from the master cylinder component 110 and a temporary stabilizing implant 130 (see FIG. 12) is installed into the osteotomy 21 by passing the temporary stabilizing implant 130 through the master cylinder component 110 opening. In the illustrated embodiment of the present invention, the temporary stabilizing implant 130 shown in FIG. 12 may have a flattened portion 132 or the like provided on its head 135 for accommodating the driving socket 142 of a driver 140 as shown in FIG. 14. The driver 140 is attached to a drill 150 (FIG. 13) at connection 141 and is used for installation of the temporary stabilizing implants 130. The driver 140 is prevented from extending completely through the master cylinder 110 by the interaction of the driver edge 143 with the master cylinder shelf 114 (see FIG. 8).

Figure 15:
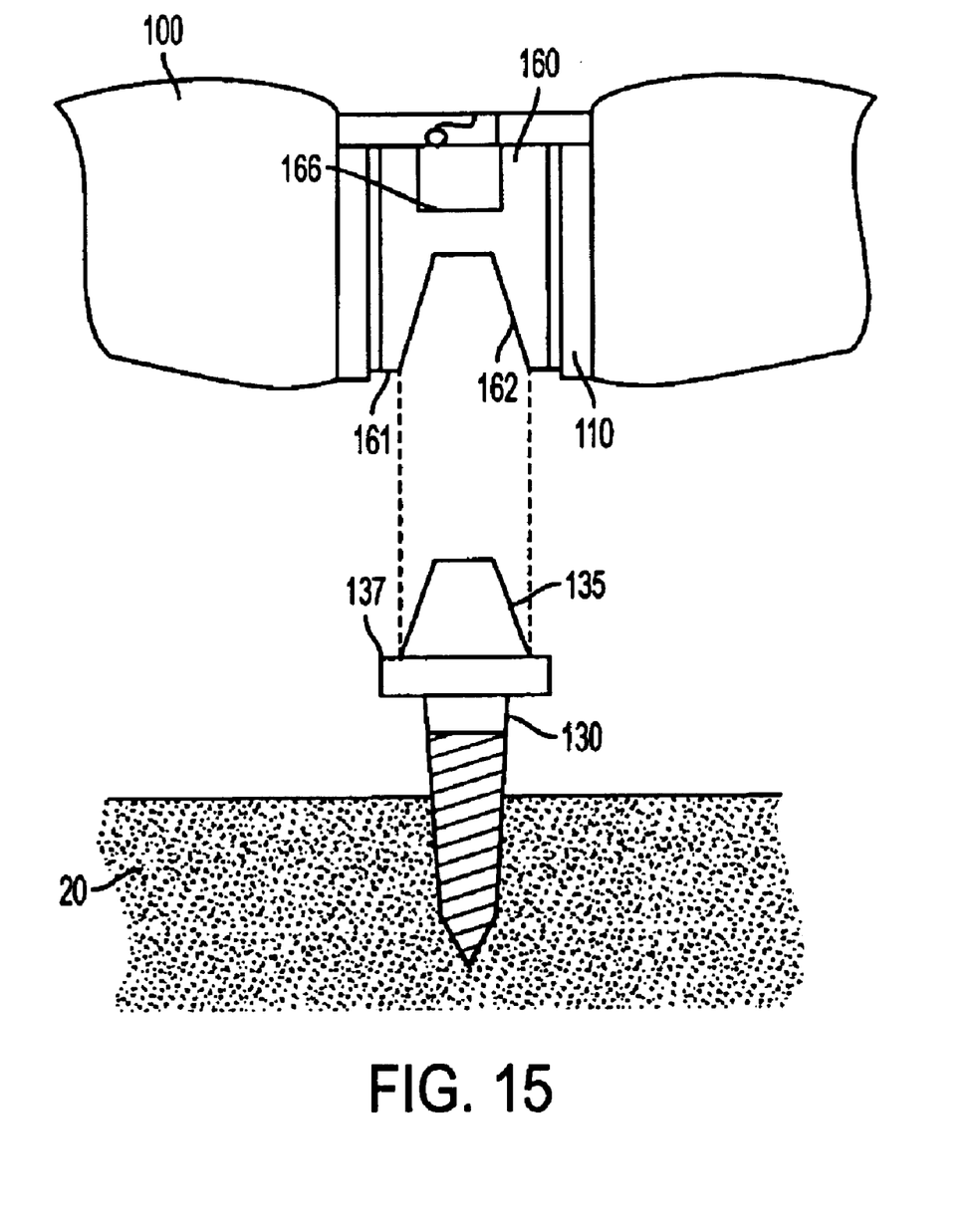
FIG. 15 illustrates the attachment of a dental surgical template to a temporary stabilizing implant.

As shown in FIG. 15, once the temporary stabilizing implants 130 are installed into a patient's jawbone 20, the master cylinder components 110 are fitted with copings 160 having sockets 162 that are adapted to enable the dental surgical template 100 to mate and engage with the heads 135 of the temporary stabilizing implants 130. The copings 160 are rotatably engaged with the master cylinder component 110 in a manner similar to the engagement of the drill guides 120 (FIG. 11), and assist in the attachment and removal of the dental template 100 from the temporary stabilizing implants 130. While the copings are removably attached to the surgical template through the use of a master cylinder component arrangement, other methods of attaching the copings or using them on a surgical template are contemplated.

Figure 16:
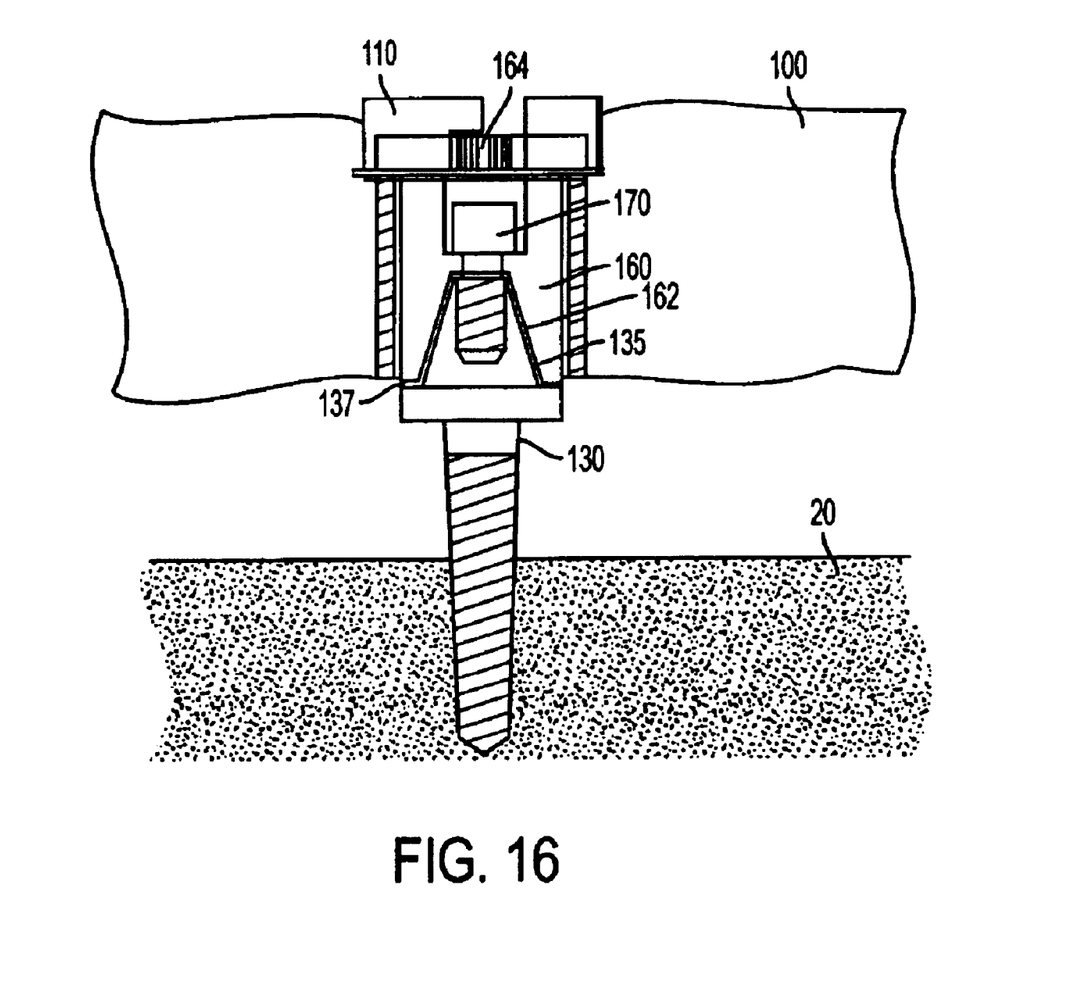
FIG. 16 is a front view of an integrated design of the master cylinder, coping, coping screw and implant.
Figure 17:
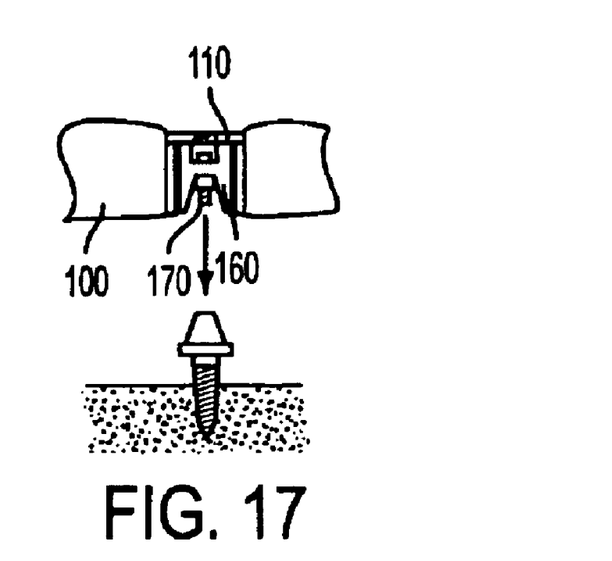
FIG. 17 is an exploded view of a template fitted with the integrated component system of FIG. 16 and adapted for engagement with a temporary stabilizing implant situated in a jawbone.

FIG. 16 illustrates the attachment and fixation of a dental template 100 to a temporary stabilizing implant 130. The coping 160, secured to the master cylinder 110 via a key 164 (see also FIG. 20) and seated within the surgical template 100, is lowered onto the head 135 of the temporary stabilizing implant 130 such that the socket 162 and head 135 mate. The temporary stabilizing implant 130 may be provided with a shelf 137 for receiving the bottom edge 161 of the coping 160 (see FIG. 15). Once the coping 160 is engaged with the temporary stabilizing implant 130, a coping screw 170, having means 172 for driving the screw 170 (e.g., an internal polygonal bore), is preferably inserted through a bore 165 in the coping 160 and into a bore 137 in the head 135 of the temporary stabilizing implant 130 to fix the surgical template 100 to the temporary stabilizing implant 130 (see FIG. 20), the screw being seated on a shelf 166 in the coping 160. Alternatively, as shown in FIG. 17, the surgical template 100 can have pre-installed an integrated component system defined by the master cylinder 110, the coping 160 and the coping screw 170, which integrated component system is then used to secured the template 100 to the temporary stabilizing implant 130. It should be appreciated that the temporary stabilizing implant 130 is installed into the jawbone 20 so that the surgical template 100 is spaced coronal to the patient's jawbone 20, i.e. spaced above the jawbone 20 and toward the crown (top portion) of a tooth. The spacing of the template 100 away from the jawbone 20 reflects the fact that the template 100 usually rests on a patient's gums and not directly on the jawbone 20. Thereafter, the surgical template 100 may be removed from the temporary stabilizing implants 130 and re-attached thereto as desired.

Figure 18:
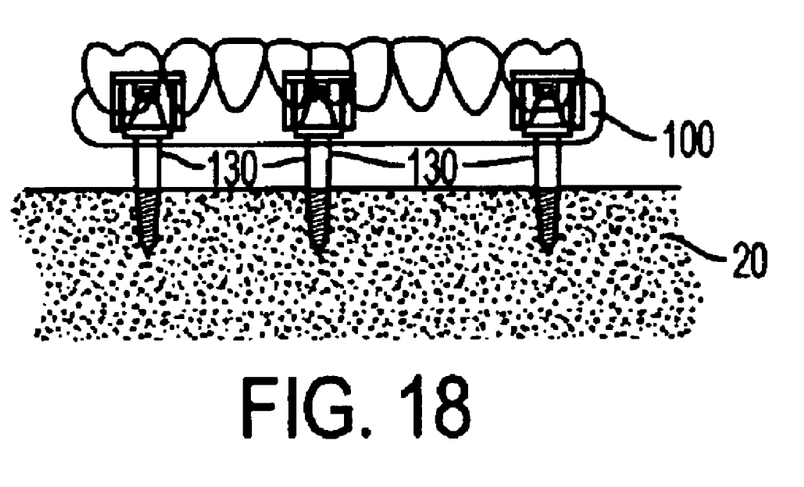
FIG. 18 illustrates a template supported by a plurality of stabilizing implants.
Figure 19:
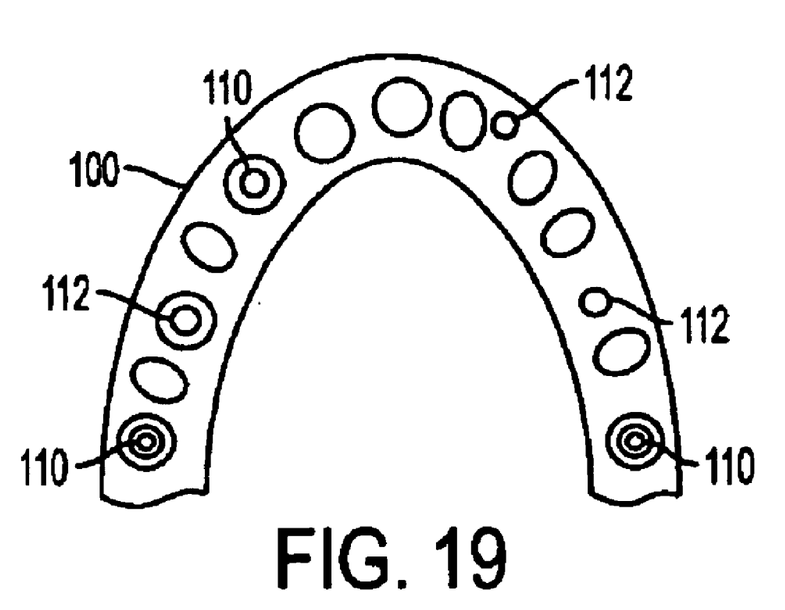
FIG. 19 illustrates a template having temporary and permanent stabilizing implant locations.
Figure 20:
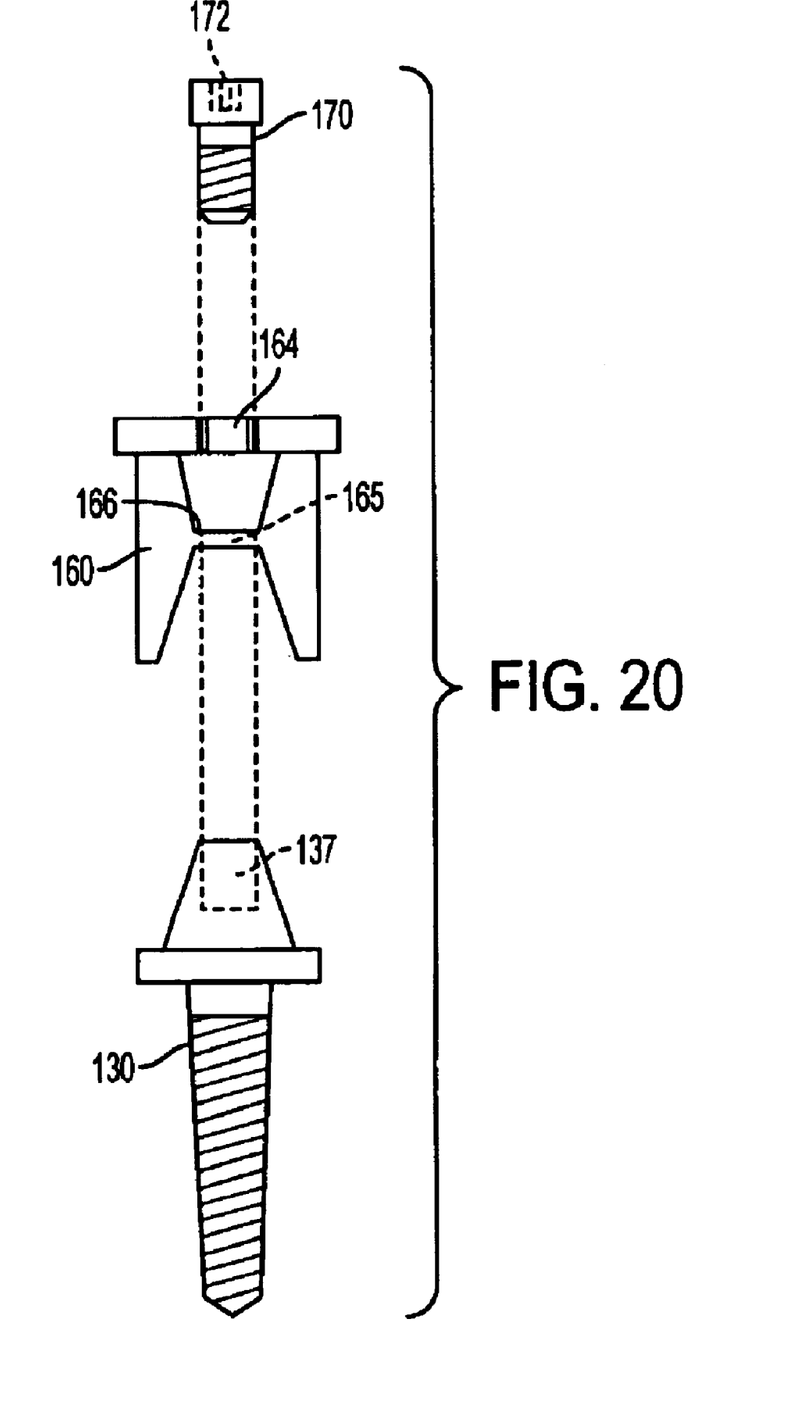
FIG. 20 illustrates an exploded view of the connection between the coping, coping screw and implant.

Once the template is fixed to the desired number of temporary stabilizing implants and properly positioned in relation to the jawbone, as shown for example in FIG. 18, the template is used as a guide to drill "permanent" implant sites 112 and install "permanent" dental implants at such sites 112 as shown for example in FIG. 19. The dental template 100 will usually already have openings at such sites 112, which openings may have drill guides fitted therein for immediate osteotomy drilling. Once osteotomies are prepared at such sites 112, "permanent" dental implants may be installed through the surgical template 100 in a manner similar to the installation of the temporary stabilizing implants through the surgical template. Should it be necessary to temporarily remove the template to gain access directly to the jawbone, removal of the coping fasteners and lifting the template from the temporary stabilizing implants is all that is required. Accurate re-introduction of the template to the temporary stabilizing implants, whether immediately or in the future, is similarly straightforward.

Should it be necessary or desired to remove a temporary stabilizing implant and replace the same with a "permanent" dental implant, the surgeon merely has to remove the temporary stabilizing implant through the opening in the surgical template, create a larger osteotomy acceptable for a permanent dental implant, and introduce a permanent dental implant through the surgical template as described above. Removal of the temporary stabilizing implant through the surgical template requires removal of the coping such that the temporary stabilizing implant can be withdrawn through the opening bounded by the master cylinder component. Alternatively, the surgical template can be removed prior to removal of the temporary stabilizing implant from the jawbone. Once the implant is removed, a drill guide may be secured to the master cylinder component to prepare the permanent implant osteotomy, such drill guide having a larger diameter than the drill guide used for the introduction of the temporary stabilizing implant. Thereafter, the permanent dental implant can be introduced to the osteotomy by passage of the implant through the master cylinder component in the surgical template. The process of replacing temporary stabilizing implants with permanent dental implants can be repeated as desired.

The temporary stabilizing implant system of the present invention thus allows a surgeon to stabilize and secure a surgical template in a specifically determined position relative to a patient's jawbone, and further allows such template to be removed and accurately re-introduced as desired. The master cylinder, coping and coping fasteners provide an environment whereby the surgical dental template may be used to create both dental implant sites and temporary/permanent dental implant installations.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

We claim:

1. A method of temporarily stabilizing a removable and replaceable dental surgical template comprising the steps of:
   a) providing a dental surgical template used for guidance in the creation of at least one permanent dental implant site in a patient's jawbone,
   b) providing at least one temporary stabilizing implant for installation into at least one temporary stabilizing implant site in a patient's jawbone,
   c) providing means in said dental surgical template for positioning said temporary stabilizing implant relative to said dental surgical template,
   d) installing said at least one temporary stabilizing implant into a patient's jawbone through said positioning means,
   e) providing means in said dental surgical template for removably engaging said dental surgical template to said at least one temporary stabilizing implant, and
   f) attaching said dental surgical template to said at least one temporary stabilizing implant with said removable engagement means such that said that dental surgical template is removable from and re-attachable to said at least one temporary stabilizing implant.

2. A method in accordance with claim 1, wherein said means for positioning said at least one temporary stabilizing implant further comprises at least one opening in at least one predetermined location relative to the at least one temporary stabilizing implant site.

3. A method in accordance with claim 2, wherein said at least one predetermined location is defined according to computer-generated data.

4. A method in accordance with claim 3, wherein said computer-generated data is derived from a CT-scan of a patient's jawbone.

5. A method in accordance with claim 2, wherein said at least one opening is adapted for the passage of said at least one temporary stabilizing implant therethrough.

6. A method in accordance with claim 2, wherein said at least one opening further comprises a master cylinder component.

7. A method in accordance with claim 6, further comprising the positioning of a drill guide within said master cylinder component for assisting in the formation of said at least one temporary stabilizing implant site.

8. A method in accordance with claim 7, further comprising the step of rotatably securing the drill guide to said master cylinder component.

9. A method in accordance with claim 6, wherein said means for removably engaging said dental surgical template further comprises a coping that is engageable with both said master cylinder component and said at least one temporary stabilizing implant.

10. A method in accordance with claim 9, wherein said coping is rotatably engageable said master cylinder component.

11. A method in accordance with claim 9, further comprising the step of securing said coping to said at least one temporary stabilizing implant.

12. A method in accordance with claim 11, further comprising the step of securing said coping to said at least one temporary stabilizing implant with a coping screw.

13. A method in accordance with claim 1, further comprising the step of installing a plurality of temporary stabilizing implants into a plurality of temporary stabilizing implant sites.

* * * * *